(12) United States Patent
Waite et al.

(10) Patent No.: US 11,878,135 B2
(45) Date of Patent: Jan. 23, 2024

(54) MATERIAL APPLICATION SYSTEM FOR TUNNELING WOUNDS THAT ALLOWS CO-DELIVERY OF SOLUTIONS

(71) Applicant: SYSTAGENIX WOUND MANAGEMENT, LIMITED, West Sussex (GB)

(72) Inventors: Alexander Waite, Cowling (GB); Carrina Ward, Gargrave (GB); Katie Bourdillon, Leeds (GB)

(73) Assignee: Systagenix Wound Management, Limited, Berkshire (GB)

( * ) Notice: Subject to any disclaimer, the term of this patent is extended or adjusted under 35 U.S.C. 154(b) by 519 days.

(21) Appl. No.: 17/270,737

(22) PCT Filed: Aug. 26, 2019

(86) PCT No.: PCT/IB2019/057159
§ 371 (c)(1),
(2) Date: Feb. 23, 2021

(87) PCT Pub. No.: WO2020/044205
PCT Pub. Date: Mar. 5, 2020

(65) Prior Publication Data
US 2021/0187259 A1 Jun. 24, 2021

Related U.S. Application Data

(60) Provisional application No. 62/723,245, filed on Aug. 27, 2018.

(51) Int. Cl.
*A61M 31/00* (2006.01)
*A61F 13/26* (2006.01)
(Continued)

(52) U.S. Cl.
CPC ....... *A61M 31/00* (2013.01); *A61F 13/00012* (2013.01); *A61F 13/2002* (2013.01); *A61F 13/266* (2013.01)

(58) Field of Classification Search
CPC .......... A61F 13/26–28; A61F 13/00012; A61F 13/2002; A61M 3/00–0295; A61M 31/00–007
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report & Written Opinion in International Application No. PCT/IB2019/057159, dated Jan. 8, 2020.
(Continued)

*Primary Examiner* — Susan S Su

(57) ABSTRACT

A medical delivery device for treating a tunneling wound includes an outer sleeve, a plunger, and a hollow tube extending through an opening in the plunger. The plunger is configured to deliver a wound treatment material from an inner cavity of the outer sleeve, through a cavity opening on the outer sleeve, and into the tunneling wound. The hollow tube is configured to deliver a fluid to the wound treatment material after insertion into the tunneling wound. In some embodiments, the medical delivery device may further include a flap disposed on the outer sleeve. The flap may be reconfigurable between a closed position in which the flap is configured to shield the cavity opening, and an open position
(Continued)

in which the flap is configured to allow the wound treatment material to be ejected through the cavity opening.

21 Claims, 4 Drawing Sheets

(51) Int. Cl.
  *A61F 13/00* (2006.01)
  *A61F 13/20* (2006.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,309,454 B1 | 10/2001 | Harvey et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 8,461,410 B2 | 6/2013 | Cullen et al. |
| 2001/0056254 A1* | 12/2001 | Cragg .............. A61B 17/0057 604/15 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2013/0237898 A1 | 9/2013 | Kirkham et al. |
| 2014/0046239 A1 | 2/2014 | Taniguchi et al. |
| 2015/0351974 A1 | 12/2015 | Levantino et al. |
| 2018/0250172 A1* | 9/2018 | Turner .............. A61F 13/2074 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |

(56) References Cited

FOREIGN PATENT DOCUMENTS

| WO | 99/13793 A1 | 3/1999 |
|---|---|---|
| WO | WO-2005/123170 A1 | 12/2005 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al.; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

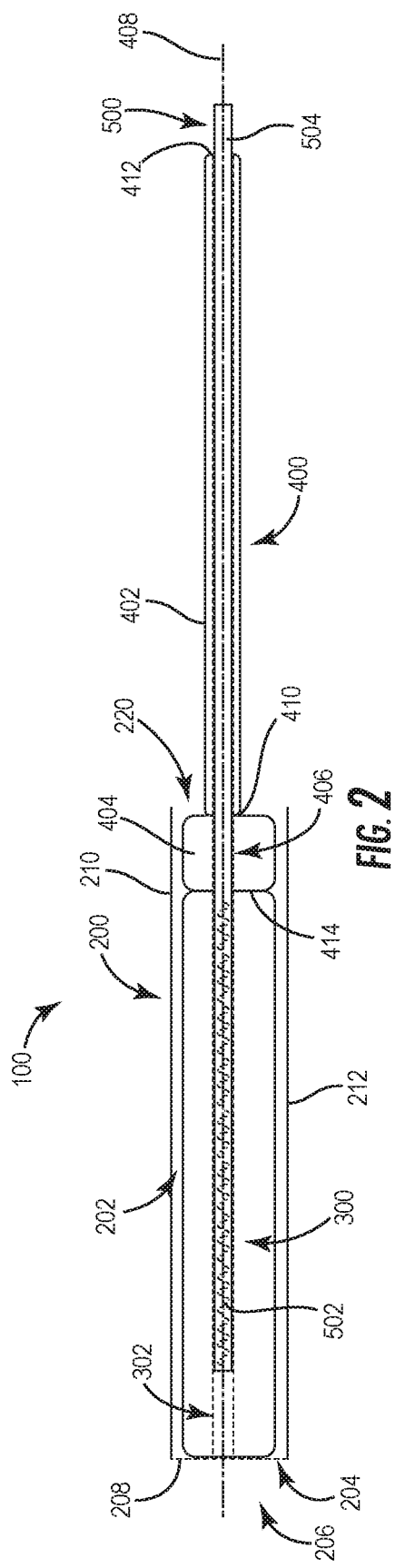
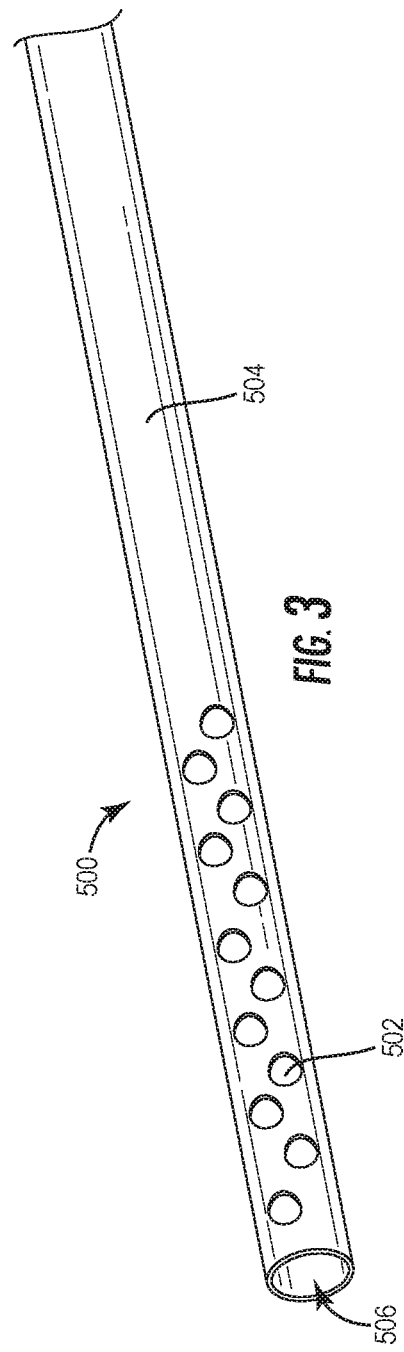
FIG. 2
FIG. 3

MATERIAL APPLICATION SYSTEM FOR TUNNELING WOUNDS THAT ALLOWS CO-DELIVERY OF SOLUTIONS

CROSS-REFERENCE TO RELATED APPLICATIONS

This Application claims the benefit of priority to international patent application number PCT/IB2019/057159, filed on Aug. 26, 2019, which claims the benefit of priority to U.S. Provisional Application No. 62/723,245, filed on Aug. 27, 2018, the complete disclosures of which are hereby incorporated herein by reference in their entireties.

BACKGROUND

The present disclosure relates generally to the delivery of treatment materials to a wound. The present disclosure relates more particularly to the delivery of treatment materials into a tunneling wound.

Tunneling wounds are secondary wounds leading off from a primary wound. Tunneling wounds typically take the form of channels that extend from the primary wound deeper into the tissue. The channels may be of an irregular shape and may split off into additional tunneling wounds. A conventional treatment for a tunneling wound includes packing the wound with absorbent materials along with an antimicrobial treatment to absorb wound exudate and medicate the wound to promote healing.

An alternative to conventional tunneling wound treatments includes using bioresorbable products, which do not need to be removed from the wound after insertion. These bioresorbable products create a healing environment within the wound. However, these products may be challenging to apply as their structure tends to rapidly break down (e.g., gel, etc.) when hydrated. Hydration may result from exposure of the products to excess moisture and/or by wound exudate before and during the delivery process. Devices and methods are desired that improve the delivery of treatment materials for tunneling wounds.

SUMMARY

One implementation of the present disclosure is a medical delivery device for treating a tunneling wound. The device includes an outer sleeve and a plunger configured to be received within a cavity of the outer sleeve. The plunger includes a shaft and a head that together define an opening extending through a central axis of the plunger. The device additionally includes a hollow tube extending through the opening and configured to deliver a fluid to a wound treatment material contained within the cavity.

In some embodiments, the outer sleeve may further include a flap disposed on an end of the outer sleeve. The flap may be reconfigurable between a closed position, in which the flap is configured to shield a cavity opening, and an open position, in which the flap is configured to allow the wound treatment material to be ejected from the cavity through the cavity opening and into the tunneling wound. In some embodiments, the flap may be configured to open upon application of a predetermined force to the flap.

In some embodiments, both the outer sleeve and the head of the plunger have a rectangular cross section normal to their central axis. In some embodiments, the wound treatment material is a freeze dried collagen material. In some embodiments, the freeze dried collagen material is provided in a rope form and includes a central axis opening configured to receive the hollow tube.

In any of the above embodiments, the hollow tube may additionally include a plurality of perforations disposed proximate to an end of the hollow tube and configured to deliver a fluid from the hollow tube to the wound treatment material along a length of the wound treatment material. The hollow tube may be configured to deliver the fluid after the wound treatment material is deposited in the tunneling wound. In some embodiments, the wound treatment material contains an active component configured to interface with the fluid delivered to the wound treatment material.

Another implementation is a method of deploying a wound treatment material into a tunneling wound. The method includes preparing a medical delivery device including an outer sleeve and a plunger. The outer sleeve defines a cavity that is configured to receive both the wound treatment material and the plunger. The method additionally includes depressing the plunger to deliver the wound treatment material from the cavity and into the tunneling wound, delivering a fluid to the wound treatment material by passing a fluid through a hollow tube passing through the plunger and inserted into the wound treatment material, and retracting the hollow tube from the wound treatment material. In some embodiments, the method may additionally include passing a head of the plunger through the cavity and past an end of the cavity, and rotating the plunger to prevent the plunger from being able to retract through the outer sleeve.

In some embodiments, the method may additionally include compressing the wound treatment material and inserting the wound treatment material into the cavity.

Another implementation is a kit for a medical delivery device used to deploy a wound treatment material into a tunneling wound. The kit includes an outer sleeve defining a cavity and a plunger configured to be received within the cavity. The plunger includes a shaft including a first shaft end and a second shaft end, a head disposed on the first shaft end, and an opening extending through a central axis of the shaft and the head. The kit includes a hollow tube that extends through the opening and one or more freeze dried collagen materials configured to fit within the cavity and around the hollow tube.

In some embodiments, a length of the hollow tube may be greater than a combined length of the plunger and 50% of the freeze dried collagen material.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

FIG. 2 is a side sectional view of a medical delivery device containing a wound treatment material, according to an exemplary embodiment.

FIG. 3 is a partial front perspective view of a hollow tube for a medical delivery device, according to an exemplary embodiment.

DETAILED DESCRIPTION

Overview

Referring generally to the FIGURES, a medical delivery device configured for use with treating tunneling wounds is provided, according to various exemplary embodiments. The device is configured to deliver a wound treatment material to a tunneling wound and to minimize exposure of the wound treatment material to exudate from surrounding wounds, entry wounds from which the tunneling wound extends, and/or an entry region of the tunneling wound. The device is configured to eject the wound treatment material from a protective sleeve or outer sleeve, through an opening in the sleeve, and directly into the tunneling wound. The device includes a plunger configured to facilitate delivery of the wound treatment material into the tunneling wound (e.g., the insertion depth of the wound treatment material into the tunneling wound, the speed of delivery, etc.). The device also includes an applicator or hollow tube configured to deliver a fluid to the wound treatment material once inserted into the tunneling wound. Among various alternatives, the fluid may be a hydrating solution or a medicant (e.g., an antimicrobial solution to promote healing, etc.).

A method for delivery of the wound treatment material includes preparing the medical delivery device for use with inserting the wound treatment material into the tunneling wound, depressing the plunger to eject the wound treatment material from a cavity defined by the protective sleeve, delivering the fluid to the wound treatment material by passing the fluid through the hollow tube, and retracting the hollow tube from the wound treatment material. The protective sleeve and the plunger for the medical delivery device may be shaped to facilitate the removal of the hollow tube from the wound treatment material without repositioning the wound treatment material. For example, a head of the plunger and an opening defined by the protective sleeve may be substantially rectangular. A method of ejecting the wound treatment material from the cavity may include depressing the plunger such that the head of the plunger passes through the opening in the sleeve and rotating the plunger by approximately 45° such that the head is prevented from being retracted back into the cavity.

The device may be provided as part of a kit including a freeze dried collagen material. The freeze dried collagen material may be configured to fit within the cavity and around the hollow tube such that any fluids passing through the hollow tube are received along an inner portion (e.g., a central portion) of the freeze dried collagen material rather than directly upon the tunneling wound. These and other features and advantages of the medical delivery device are described in detail below.

Medical Delivery Device Construction

Figure 1:
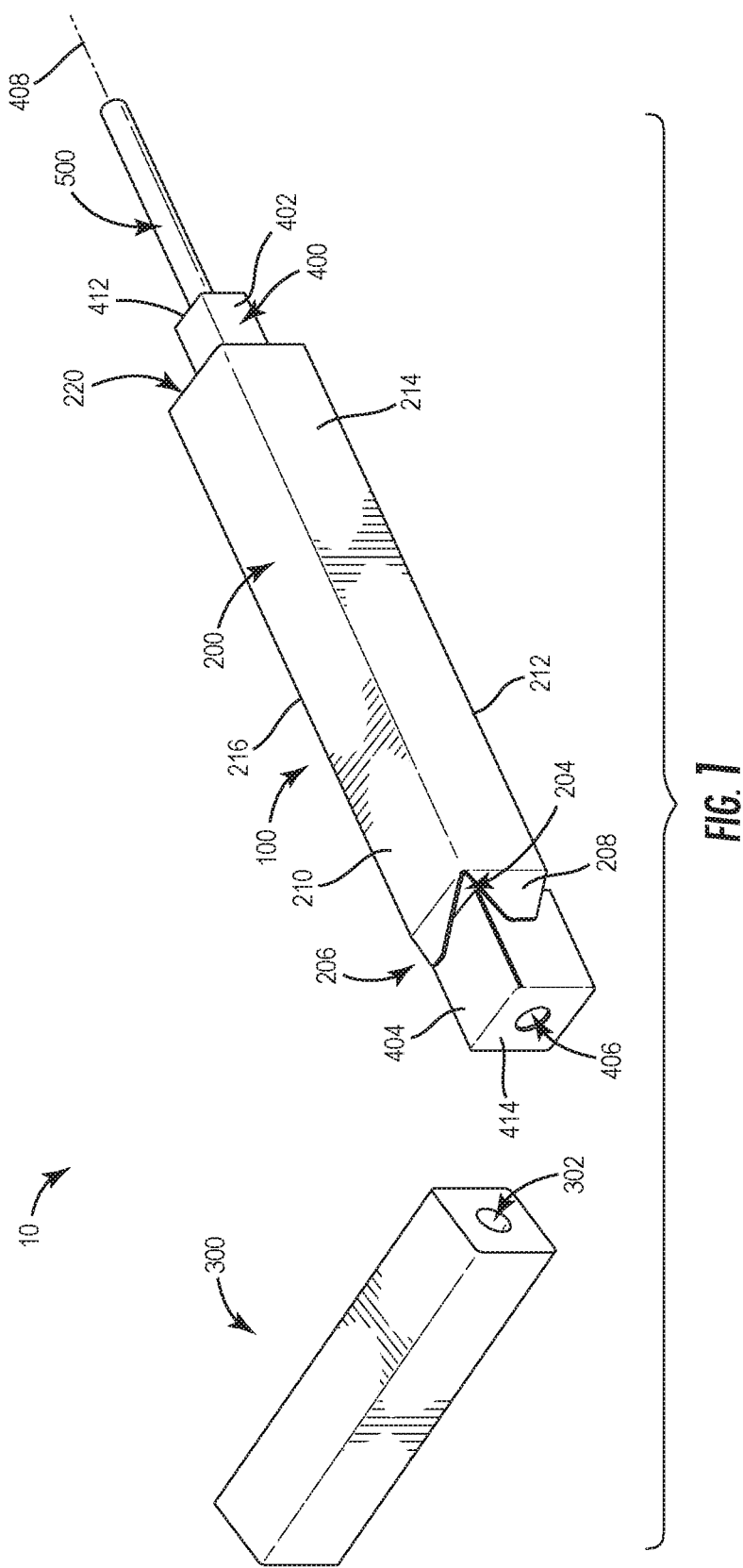
FIG. 1 is front perspective view of a kit for medical delivery device used deploy a wound treatment material into a tunneling wound, according to an exemplary embodiment.

Referring now to FIGS. 1-3, a medical delivery device 100 is shown, according to an exemplary embodiment. FIG. 1 shows the medical delivery device 100 configured as part of a kit 10 used for the treatment of tunneling wounds. The kit includes at least one wound treatment material 300, which is shown separated from the delivery device 100 in FIG. 1. The wound treatment material 300 is configured in the shape of a rectangular cuboid whose cross-section, normal to a longitudinal axis of the wound treatment material 300, is substantially square.

FIG. 2 shows a cross-section through a side of a delivery device 100, which is configured in preparation for the treatment of a tunneling wound. As shown in FIGS. 1-2, the delivery device 100 includes an outer sleeve 200 defining an inner cavity 202 within which the wound treatment material 300 is received. A cavity opening, shown as first cavity opening 204 is disposed in a first end 206 of the outer sleeve 200. The first cavity opening 204 may be covered or shielded by one or more flaps 208, which are configured to prevent the wound treatment material 300 from being accidentally ejected from the outer sleeve 200. The one or more flaps 208 also shield the wound treatment material 300 from the environment surrounding the outer sleeve 200.

As shown in FIG. 2, the delivery device 100 includes a plunger 400 configured to engage with the wound treatment material 300. The plunger 400 is received within the cavity 202 of the outer sleeve 200 and positioned in contact with an end of the wound treatment material 300 (i.e., an end of the wound treatment material 300 opposite the first cavity opening 204). In the embodiment of FIG. 2, the position of the wound treatment material 300 within the inner cavity 202 is adjustable and may be modified by depressing the plunger 400 further into the inner cavity 202 and toward the first cavity opening 204.

In the embodiment of FIGS. 1-2, the plunger 400 includes a shaft 402 and a head 404 coupled thereto. The geometry of the head 404 of the plunger 400 is substantially similar to both the geometry of the wound treatment material 300 and the geometry of the first cavity opening 204. This allows the head 404 to fully interface with the wound treatment material 300 while also preventing the wound treatment material 300 from bypassing the plunger 400.

As shown in FIGS. 1-2, the plunger 400 includes an opening 406 extending through a central axis 408 of the plunger 400 (i.e., through both the head 404 of the plunger 400 and the shaft 402). The opening 406 is configured to receive a hollow tube 500 configured to deliver a fluid to the wound treatment material 300. As shown in FIG. 2, the hollow tube 500 extends beyond the plunger 400 and into the wound treatment material 300 such that the fluid may be delivered to an inner portion of the wound treatment material 300. As shown in FIGS. 2-3, the hollow tube 500 includes a plurality of perforations 502 that extend through a wall 504 of the hollow tube 500 proximate to the wound treatment material 300, which allow the hollow tube 500 to dispense the fluid along a length of the wound treatment material 300.

Outer Sleeve

An exemplary embodiment of an outer sleeve 200 for the delivery device 100 is shown in FIGS. 1-2. The outer sleeve 200 is made from a single piece of non-permeable material formed in the shape of a rectangular cuboid (i.e., a right rectangular prism having identical cross-sections normal to a central axis of the sleeve 200). In other implementations, the shape of the outer sleeve 200 may be different (e.g., the outer sleeve 200 may be formed in the shape of a cylinder, etc.). In some embodiments, the outer sleeve 200 is made from a plastic material such as medical grade polyethylene, polycarbonate, etc. In other embodiments, the outer sleeve 200 is made from another suitable non-permeable material. Among other benefits, using a non-permeable material prevents water and/or wound exudate from penetrating the surfaces of the outer sleeve 200.

As shown in FIG. 2, the outer sleeve 200 is configured as a shell including an upper wall 210, a lower wall 212, and side walls 214, 216 (also see FIG. 1) that together define an inner cavity 202. The inner cavity 202 is configured to receive at least one wound treatment material 300 and a plunger 400. As shown in FIGS. 1-2, the inner cavity 202 has a cross-sectional geometry, in a direction substantially perpendicular to the longitudinal axis of the inner cavity 202, that is similar to a cross-sectional geometry of the wound treatment material 300 and/or the head 404 of the plunger 400 (e.g., a square). Among other benefits, this configuration minimizes the unoccupied volume of the outer sleeve 200 and the amount of wound treatment material 300 that may be administered into the tunneling wound for a given device 100 size.

The outer sleeve 200 additionally defines an opening at each end of the inner cavity 202, shown as first cavity opening 204 and second cavity opening 220. Each of the first cavity opening 204 and the second cavity opening 220 have substantially the same cross-sectional shape as the inner cavity 202 (e.g., a square). In the embodiment of FIGS. 1-2, the first cavity opening 204 is configured to receive the wound treatment material 300, while the second cavity opening 220 is configured to receive the head 404 of the plunger 400. A length of the outer sleeve parallel to the longitudinal axis of the inner cavity 202 is greater than a combined length of the wound treatment material 300 and the head 404 of the plunger 400.

The outer sleeve 200 may additionally include one or more flaps 208 disposed on an end of the outer sleeve 200. In the embodiment of FIGS. 1-2, four flaps 208 are disposed on the outer sleeve 200. Each one of the flaps 208 is hingedly coupled to one of the upper wall 210, lower wall 212, or one of the side walls 214, 216. In an embodiment, each flap 208 is formed as part of the outer sleeve 200 (e.g., injection molded or otherwise formed with the outer sleeve 200 as a single piece of material). In other embodiments, each flap 208 is a separate piece of material from the outer sleeve 200 and is permanently affixed (e.g., welded, glued, etc.) to the outer sleeve 200.

Each one of the flaps 208 is reconfigurable between an open position, in which the flap 208 is configured to allow the wound treatment material 300 to be ejected from the inner cavity 202 through the first cavity opening 204, and a closed position, in which the flap 208 is configured to shield the first cavity opening 204. In the embodiment of FIGS. 1-2, each of the flaps 208 is shaped such that, in the closed position, the flaps 208 contact one another and completely block off the first cavity opening 204. Among other benefits, in the closed position the flaps 208 prevent any moisture from the environment surrounding the outer sleeve 200 from penetrating through the outer sleeve 200 and into the wound treatment material 300. In alternative embodiments, the flaps 208 may be configured to only partially occlude the first cavity opening 204 in the closed position. For example, the flaps 208 may only shield the wound treatment material 300 around a perimeter of the wound treatment material 300 (e.g., near surfaces of the wound treatment material 300 that are in contact with the outer sleeve 200), and thereby limit the amount of gelling or structural degradation of the wound treatment material 300 prior to insertion of the wound treatment material 300 into the tunneling wound.

The flaps 208 are configured to move from the closed position to the open position upon application of a predetermined force to the flaps 208. To secure the flaps 208 over the first cavity opening 204 in the closed position, the flaps 208 may be folded over one another, interlocked with one another, or configured to removably engage with the outer sleeve 200. In an exemplary embodiment, one or more flaps 208 may include a slot that is configured to engage with another flap 208 in the closed position. In other embodiments, the outer sleeve 200 may include features (e.g., slots, clips, etc.) configured to receive one or more flaps 208 in the closed position. In yet other embodiments, one or more flaps 208 may be removably coupled to one another using an adhesive product in the closed position.

Plunger

A plunger 400 for the medical delivery device 100 is shown in FIGS. 1-2, according to an exemplary embodiment. The plunger 400 is configured to reposition the wound treatment material 300 relative to the outer sleeve 200 during delivery of the wound treatment material into the tunneling wound. The plunger 400 includes a shaft 402 and a head 404 coupled thereto. As shown in FIG. 2, the shaft 402 includes a first shaft end 410 and a second shaft end 412. The head 404 is disposed to the first shaft end 410. The head 404 may be formed with the shaft 402 as a single piece of material (e.g., via an injection molding process) or coupled to the first shaft end 410 (e.g., via gluing, welding, a clip feature, and/or a threaded interface between the head 404 and the shaft 402). The plunger 400 may be made from a variety of different materials including medical grade polyethylene, polycarbonate, etc. In some embodiments, the plunger 400 is made from a similar material as the outer sleeve 200.

As shown in FIG. 2, the head 404 of the plunger 400 is received within the second cavity opening 220 of the outer sleeve 200. The head 404 of the plunger 400 has a cross-sectional shape normal to a central axis 408 of the plunger 400 that is similar to a cross-sectional shape of the wound treatment material 300 and/or the inner cavity 202 of the outer sleeve 200 (e.g., a square). A length and width of the head 404, normal to the central axis of the plunger 400, are dimensioned to fill the space of the inner cavity 202, while also permitting the head 404 to slide freely along a length of the inner cavity 202. This configuration prevents the wound treatment material 300 from being forced through any gaps between the perimeter surfaces of the head 404 and the outer sleeve 200, while also preventing the head 404 from becoming lodged or stuck in a single position within the outer sleeve 200 during operation. As shown in FIG. 2, a forward surface 414 of the head 404 is configured to contact the wound treatment material 300.

The plunger 400 includes an opening 406 extending along a full length of the plunger 400 parallel to its central axis 408. In the embodiment of FIG. 2, the central axis 408 of the plunger 400 is located in the same position as a central axis for the shaft 402 and the head 404 of the plunger 400. The opening 406 is configured to receive the hollow tube 500 for the medical delivery device 100. In the embodiment of FIG. 2, the opening 406 has a cross-sectional geometry that is similar to a cross-sectional geometry of the hollow tube 500 (e.g., circular). As shown in FIG. 2, the opening 406 is alignable with a corresponding opening, shown as central axis opening 302, in the wound treatment material 300.

The shaft 402 of the plunger 400 extends through the second cavity opening 220 of the outer sleeve 200. The shaft 402 may be manipulated by a user to reposition the plunger 400 with respect to the outer sleeve 200. A length of the shaft 402, in a direction substantially parallel to the central axis of the plunger 400, is greater than a combined length of the outer sleeve and the head 404 of the plunger 400 (i.e., the length of the shaft 402 is sufficient to allow the user to push the head 404 of the plunger 400 through an entire length of the inner cavity 202 and beyond the first cavity opening 204).

The shaft 402 may be configured in a variety of different shapes. For example, the shaft 402 may be cylindrical, triangular, etc. In the embodiment of FIG. 2, the shaft 402 is configured in the shape of a rectangular cuboid whose outer surfaces are substantially parallel to the walls 210, 212, 214, 216 of the outer sleeve 200. Among other benefits, the orientation of the outer surfaces of the shaft 402 relative to the walls 210, 212, 214, 216 of the outer sleeve 200 may be used as a visual guide enabling a user to approximate a rotational position of the head 404 relative to the outer sleeve 200. The shaft 402 may also include ergonomic features (e.g., contoured surfaces, etc.) and/or a position indicator (e.g., indicator marks along an outer surface of the shaft 402, etc.) to facilitate repositioning of the shaft by the user.

Hollow Tube

A hollow tube 500 for the medical delivery device 100 is shown in FIGS. 2-3, according to an exemplary embodiment. The hollow tube 500 may be formed in a variety of different shapes and sizes, depending on the desired characteristics of the medical delivery device 100. As shown in FIG. 3, a cross-sectional geometry of the hollow tube 500, in a direction substantially perpendicular to a primary axis of the hollow tube 500, is similar to the cross-sectional geometry of the opening 406 in the plunger 400 (e.g., circular). As shown in FIG. 2, the length of the hollow tube 500, in a direction oriented substantially parallel to a primary axis of the hollow tube 500, is greater than a combined length of the plunger 400 and 50% of a length of the wound treatment material 300. An outer diameter of the hollow tube 500 is dimensioned slightly smaller than the inner diameter of the opening 406 in the plunger 400 to allow the hollow tube 500 to move freely with respect to the plunger 400 during operation.

The hollow tube 500 is configured to deliver a fluid through the device 100 and into the wound treatment material 300. The fluid may be one or a combination of a hydrating solution to wet an interior portion of the wound treatment material 300 (e.g., to facilitate gelling of the wound treatment material 300 onto the surfaces of the tunneling wound) and a medicant such as an antimicrobial solution. In an exemplary embodiment, the hollow tube 500 is configured to provide a wound irrigation solution such as Prontasan to the wound treatment material 300. In another embodiment, the hollow tube 500 is configured to provide a solution configured to interact and/or react with one or more active components in the wound treatment material 300 (e.g., the solution could contain glucose, which could interact with glucose oxidase in the wound treatment material 300 to generate hydrogen peroxide, etc.).

As shown in FIG. 3, the fluid is discharged from the hollow tube 500 into an inner portion of the wound treatment material 300 through an opening, shown as end opening 506. The hollow tube 500 additionally includes a plurality of perforations 502 that extend through a wall 504 of the hollow tube 500. As shown in FIGS. 2-3, the perforations 502 are located proximate to an end of the hollow tube 500 that is configured to be received within the inner portion of the wound treatment material 300 (i.e., an end of the hollow tube 500 proximate to the end opening 506). The pitch, size, and shape of each perforation 502 may be different depending on the desired flow rate and distribution along a length of the wound treatment material 300. In the embodiment of FIGS. 2-3, the perforations 502 are configured as circular holes of uniform diameter. In other embodiments, the diameter of the perforations may vary along the length of the hollow tube 500 (e.g., starting small near an end of the wound treatment material 300 and getting larger moving toward an opposing end of the wound treatment material 300 to promote flow uniformity along the length of the hollow tube 500). In yet other embodiments, the shape of each of the perforations 502 may be different along the length of the hollow tube 500.

Wound Treatment Material

A wound treatment material 300 configured for delivery by the medical delivery device 100 is shown in FIGS. 1-2, according to an exemplary embodiment. Among other functions, the wound treatment material 300 provides a wound filler to support the tunneling wound and thereby prevent the tunneling wound from being deformed while a patient is moving. The wound treatment material 300 may also be used to help manage wound conditions such as moisture, pH, protease activity, bioburden, etc. Advantageously, the wound treatment material 300 may be bioresorbable, which eliminates the need to remove the material 300 from the tunneling wound at a later time after treatment.

Similar to the outer sleeve 200 and the head 404 of the plunger 400, the wound treatment material 300 is configured in the shape of a rectangular cuboid having uniform cross-section along its length. A cross-sectional geometry of the wound treatment material 300, normal to a central axis for the wound treatment material 300, is approximately the same as the cross-sectional geometry of the inner cavity 202 and the head 404 of the plunger 400. In the embodiment of FIG. 2, a width and a length of the wound treatment material 300, normal to the central axis of the wound treatment material 300, is slightly smaller than a corresponding height and width of the inner cavity 202 such that the wound treatment material 300 completely fills the cavity into which it is inserted. In other embodiments, the wound treatment material 300 may be compressed prior to insertion into the outer sleeve 200 and configured to expand in dimension when exposed to a fluid (e.g., a hydrating solution and/or a medicant). In this latter embodiment, the wound treatment material may expand after delivery into the tunneling wound to better fill and protect the wound site.

As shown in FIG. 2, the wound treatment material 300 is provided in a rope form and includes a central axis opening 302 configured to receive the hollow tube 500 of the delivery device 100. A length of the wound treatment material 300 may vary depending on the size (e.g., depth) of the tunneling wound. For example, the length of the wound treatment material 300 may be approximately equal to the depth of the tunneling wound, etc. As shown in FIG. 2, the length of the wound treatment material 300 is less than the length of a portion of the outer sleeve 200 contained between the forward surface 414 of the head 404 of the plunger 400 and the first cavity opening 204.

The central axis opening 302 extends throughout the length of the wound treatment material 300 and provides access to an inner portion and/or a central portion of the wound treatment material 300. The central axis opening 302 may be configured in a variety of different shapes. In the embodiment of FIGS. 1-2, the central axis opening 302 is cylindrical with a circular cross-section normal to the central axis of the wound treatment material 300. As shown in FIG. 2, the central axis opening 302 has a diameter that is slightly larger than the outer diameter of the hollow tube 500, which allows the hollow tube 500 to slide freely along a length of the wound treatment material 300.

In an exemplary embodiment, the wound treatment material 300 is composed of a freeze dried collagen material (i.e., an oxidized regenerated cellulose/collagen (ORC) or collagen/ORC/silver-ORC) such as Promogran or Prisma. The wound treatment material 300 may additionally contain active components such as antimicrobials, antioxidants, and/ or anti-inflammatories to enhance the healing benefits of the material 300. The wound treatment material 300 may alternatively or additionally contain active components that are configured to interact with and/or react with a fluid delivered by the hollow tube 500 to wound treatment material 300. For example, the wound treatment material 300 may contain glucose oxidase, which interacts with glucose to generate hydrogen peroxide.

Delivery of Wound Treatment Material

A method of deploying a wound treatment material 300 into a tunneling wound 20 is illustrated in FIGS. 4A-4F, according to an exemplary embodiment. The method includes preparing a medical delivery device 100 for use in inserting the wound treatment material 300 into the tunneling wound 20. The method of preparation may include inserting the wound treatment material 300 into an inner cavity 202 of an outer sleeve 200 for the medical delivery device 100 through one of a first cavity opening 204 and a second cavity opening 220. A plurality of flaps 208 may be reconfigured into a closed position such that the flaps 208 at least partially shield the wound treatment material 300 from an environment surrounding the outer sleeve 200 (e.g., from external moisture, exudate from surrounding wounds, and/or entry wounds from which the tunneling wound 20 extends). The method of preparation may further include inserting a plunger 400 through the second cavity opening 220 such that a head 404 (see also FIGS. 1-2) of the plunger 400 is brought into contact with the wound treatment material 300. The method of preparation may also include inserting a hollow tube 500 through an opening 406 in the plunger 400 and a central axis opening 302 in the wound treatment material 300.

Figure 4A:
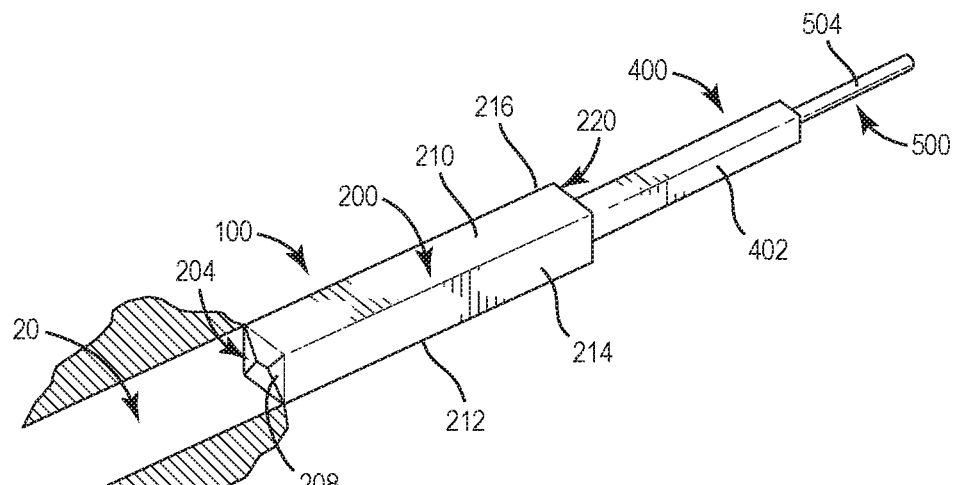
FIGS. 4A-4F are front perspective views of a medical delivery device illustrating the delivery of a wound treatment material into a tunneling wound, according to exemplary embodiments.

As shown in FIG. 4A, the method of preparation includes placing an end of the outer sleeve 200 (e.g., an end of the sleeve 200 proximate to the flaps 208 and the first cavity opening 204) at an entrance to the tunneling wound.

In various alternative embodiments, the method of preparing the device 100 may further include compressing the wound treatment material 300 and inserting the wound treatment material 300 into the inner cavity 202 of the outer sleeve 200.

Figure 4B:
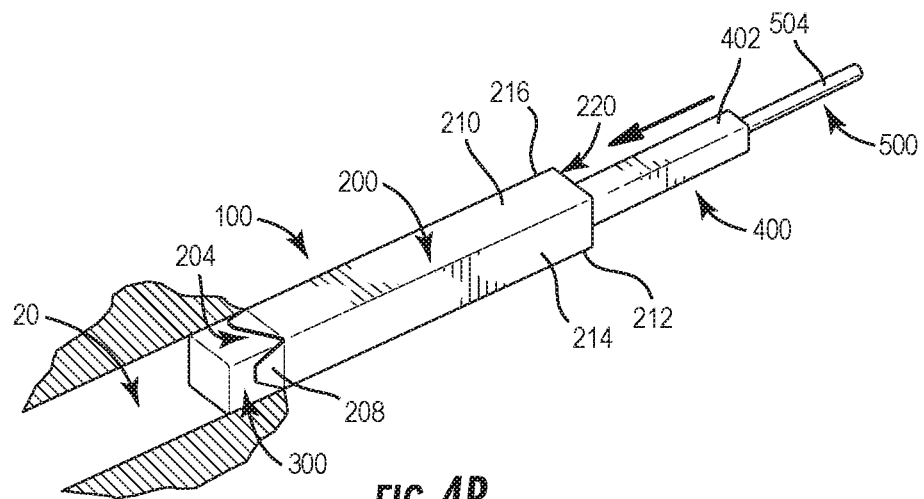

The method of deploying the wound treatment material 300 includes depressing the plunger 400 to deliver the wound treatment material 300 from the inner cavity 202 and into the tunneling wound 20. As shown in FIG. 4B, the plunger 400 is depressed toward the tunneling wound 20 against the wound treatment material 300, which presses against the flaps 208 shielding the first cavity opening 204. Upon application of a predetermined force to the flaps 208 by the wound treatment material 300, the flaps 208 begin to rotate away from the first cavity opening 204 and toward an open position. As the flaps 208 separate, the wound treatment material 300 emerges from the outer sleeve 200 and into the entrance of the tunneling wound 20. During this process, the flaps 208 effectively extend the length of the outer sleeve 200 into the entrance of the tunneling wound 20, further shielding the wound treatment material 300 from wound exudate.

Figure 4C:
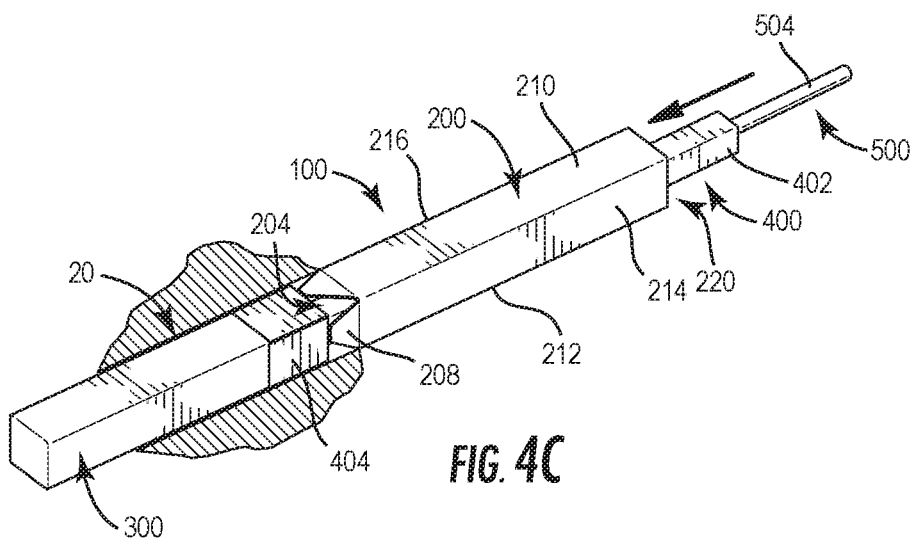

The operation of depressing the plunger 400 continues until the wound treatment material 300 is completely inserted into the tunneling wound 20. As shown in FIG. 4C, the plunger 400 is depressed a sufficient distance toward the tunneling wound 20 that the head 404 of the plunger 400 is extended just beyond the flaps 208 (i.e., such that the head 404 of the plunger 400 clears the flaps 208). In this position, the flaps 208 may be allowed to at least partially retract toward the first cavity opening 204. In other embodiments, the flaps 208 may remain fixed in position during this operation. The wound treatment material 300 remains coupled to the medical delivery device 100 via the hollow tube 500, which runs along the length of the plunger 400 and extends through at least a portion the wound treatment material 300.

The method of deployment further includes delivering a fluid to the wound treatment material 300 by passing the fluid through the hollow tube 500. This operation allows fluid to be introduced into an inner portion of the wound treatment material 300. The fluid may provide a form of hydration to the wound treatment material 300 or serve as a medicant (e.g., an antimicrobial solution such as Prontasan) to promote healing of the tunneling wound 20.

Figure 4D:
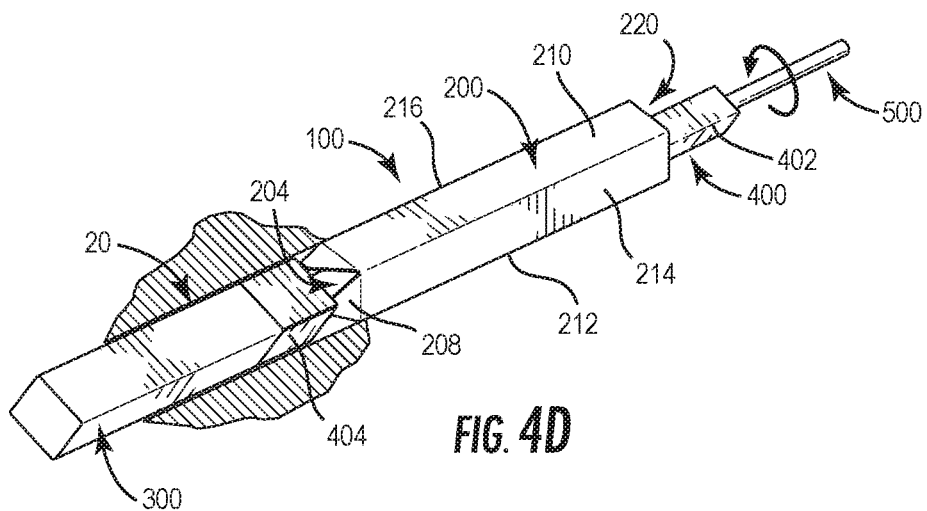
Figure 4E:
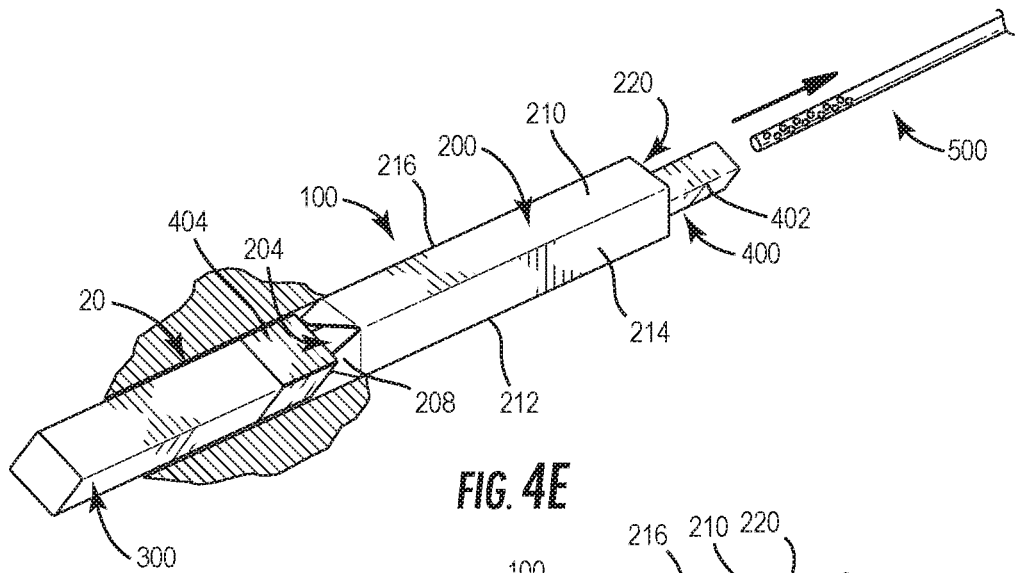
Figure 4F:
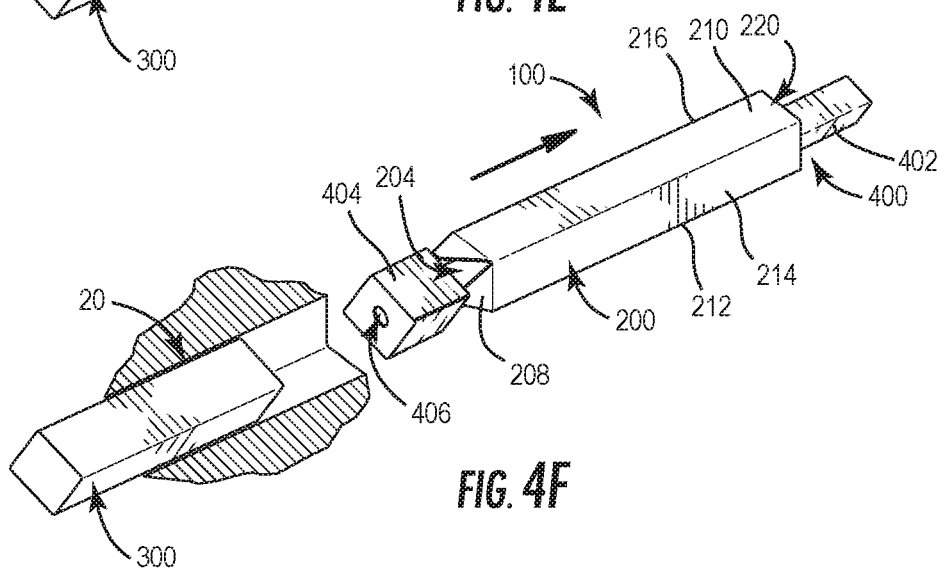

The method of deployment additionally includes retracting the hollow tube 500 from the wound treatment material 300. A method for retracting the hollow tube 500 from the wound treatment material 300 as illustrated in FIGS. 4D-4F, according to an exemplary embodiment. As shown in FIG. 4D, both the outer sleeve 200 and the head 404 of the plunger 400 have a substantially rectangular cross-section normal to a feed direction for the wound treatment material 300. The plunger 400 may be secured in position relative to the outer sleeve 200 by rotating the plunger 400 by a suitable angle. Among other benefits, rotating the head 404 of the plunger 400 prevents the wound treatment material 300 from moving or becoming dislodged from the tunneling wound 20 when retracting the hollow tube 500.

In the embodiment of FIG. 4D, the plunger 400 is rotated by approximately 45° such that a surface of the plunger 400 contacts each of the flaps 208 of the outer sleeve 200. Note that the angle of rotation used to prevent the head 404 from retracting back into the outer sleeve 200 may vary depending on the geometry of the head 404 and the outer sleeve 200. As shown in FIG. 4E, once the plunger 400 is secured in position the hollow tube 500 may be completely retracted from both the wound treatment material 300 and the plunger 400.

As shown in FIG. 4F, the method of deployment may further include removing the medical delivery device 100 from the entrance to the tunneling wound 20 by pulling on the shaft 402 of the plunger 400.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A medical delivery device for treating a tunneling wound comprising:
   an outer sleeve defining a cavity configured to hold a wound treatment material;

a plunger configured to be received within the cavity and configured to deliver the wound treatment material from the cavity and into the tunneling wound, the plunger comprising:
  a shaft comprising a first shaft end and a second shaft end;
  a head disposed on the first shaft end; and
  an opening extending through a central axis of both the shaft and the head; and
a hollow tube extending through the opening, the hollow tube configured to deliver a fluid to the wound treatment material.

2. The medical delivery device of claim 1, wherein the outer sleeve further comprises a flap disposed on an end of the outer sleeve, the flap reconfigurable between:
  a closed position in which the flap is configured to shield a cavity opening; and
  an open position in which the flap is configured to allow the wound treatment material to be ejected from the cavity through the cavity opening and into the tunneling wound.

3. The medical delivery device of claim 2, wherein the flap is configured to move to the open position upon application of a predetermined force to the plunger.

4. The medical delivery device of claim 1, wherein both the outer sleeve and the head of the plunger have a rectangular cross section normal to the central axis.

5. The medical delivery device of claim 1, wherein the wound treatment material is a freeze dried collagen material.

6. The medical delivery device of claim 5, wherein the freeze dried collagen material is provided in a rope form and includes a central axis opening configured to receive the hollow tube.

7. The medical delivery device of claim 6, the hollow tube further comprising a plurality of perforations that extend through a wall of the hollow tube, wherein the plurality of perforations are located proximate to an end of the hollow tube and configured to deliver the fluid along a length of the freeze dried collagen material.

8. The medical delivery device of claim 7, wherein the hollow tube is configured to deliver the fluid after the freeze dried collagen material is deposited in the tunneling wound.

9. The medical delivery device of claim 1, wherein the wound treatment material contains an active component configured to interact with the fluid delivered to the wound treatment material.

10. A method of deploying a wound treatment material into a tunneling wound, the method comprising:
  preparing a medical delivery device for use in inserting the wound treatment material into the tunneling wound, the medical delivery device comprising:
    an outer sleeve defining a cavity;
    a plunger configured to be received within the cavity, the plunger comprising:
      a shaft including a first shaft end and a second shaft end;
      a head disposed on the first shaft end; and
      an opening extending through a central axis of the shaft and the head; and
    a hollow tube extending through the opening;
  depressing the plunger to deliver the wound treatment material from the cavity and into the tunneling wound;
  delivering a fluid to the wound treatment material by passing the fluid through the hollow tube; and
  retracting the hollow tube from the wound treatment material.

11. The method of claim 10, wherein both the outer sleeve and the head of the plunger have a substantially rectangular cross-section normal to the central axis.

12. The method of claim 11, wherein depressing the plunger to deliver the wound treatment material into the tunneling wound comprises:
  passing the head of the plunger through the cavity and past an end of the cavity; and
  rotating the plunger by approximately 45° to prevent the plunger from being able to retract through the outer sleeve while retracting the hollow tube.

13. The method of claim 10, wherein preparing the medical delivery device further comprises:
  compressing the wound treatment material; and
  inserting the wound treatment material into the cavity.

14. The method of claim 10, wherein the outer sleeve of the medical delivery device further comprises a flap disposed on an end of the outer sleeve and reconfigurable between:
  a closed position in which the flap is configured to shield a cavity opening; and
  an open position in which the flap is configured to allow the wound treatment material to be ejected from the cavity through the cavity opening.

15. The method of claim 10, wherein the wound treatment material comprises a freeze dried collagen material.

16. A kit for a medical delivery device used to deploy a wound treatment material into a tunneling wound comprising:
  an outer sleeve defining a cavity;
  a plunger configured to be received within the cavity, the plunger comprising:
    a shaft including a first shaft end and a second shaft end;
    a head disposed on the first shaft end; and
    an opening extending through a central axis of the shaft and the plunger;
  a hollow tube extending through the opening and configured to deliver a fluid to the wound treatment material; wherein
  the wound treatment material is a freeze dried collagen material configured to fit within the cavity and around the hollow tube.

17. The kit of claim 16, the outer sleeve further comprising a flap disposed on an end of the outer sleeve, wherein the flap is reconfigurable between:
  a closed position in which the flap is configured to shield a cavity opening; and
  an open position in which the flap is configured to allow the freeze dried collagen material to be ejected from the cavity through the cavity opening.

18. The kit of claim 17, wherein the flap is configured to move to the open position upon application of a predetermined force to the plunger.

19. The kit of claim 16, the hollow tube further comprising a plurality of perforations that extend through a wall of the hollow tube, wherein the plurality of perforations are located proximate to an end of the hollow tube and configured to deliver the fluid from the hollow tube along a length of the freeze dried collagen material.

20. The kit of claim 19, wherein a length of the hollow tube is greater than a combined length of the plunger and 50% of a length of an individual one of the freeze dried collagen material.

21. The kit of claim 16, wherein the freeze dried collagen material contains an active component configured to interact with the fluid delivered to the freeze dried collagen material.

\* \* \* \* \*